(12) United States Patent
Kurohara

(10) Patent No.: US 10,918,538 B2
(45) Date of Patent: Feb. 16, 2021

(54) ABSORBENT ARTICLE AND METHOD OF MANUFACTURING THE SAME

(71) Applicant: DAIO PAPER CORPORATION, Ehime (JP)

(72) Inventor: Takeshi Kurohara, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 697 days.

(21) Appl. No.: 15/549,731

(22) PCT Filed: Mar. 4, 2016

(86) PCT No.: PCT/JP2016/056748
§ 371 (c)(1),
(2) Date: Aug. 9, 2017

(87) PCT Pub. No.: WO2016/140341
PCT Pub. Date: Sep. 9, 2016

(65) Prior Publication Data
US 2018/0014986 A1    Jan. 18, 2018

(30) Foreign Application Priority Data
Mar. 4, 2015    (JP) .................................. 2015-042069

(51) Int. Cl.
*A61F 13/84* (2006.01)
*D21H 21/14* (2006.01)
(Continued)

(52) U.S. Cl.
CPC .... *A61F 13/8405* (2013.01); *A61F 13/15617* (2013.01); *A61F 13/15626* (2013.01);
(Continued)

(58) Field of Classification Search
CPC ...... D21H 27/002; D21H 21/14; D21H 23/04; D21H 23/22; D21H 23/28; D21H 27/00;
(Continued)

(56) References Cited

U.S. PATENT DOCUMENTS 2,884,147 A * 4/1959 Hunt ........................ B63B 27/24
                                                          406/38
4,245,689 A * 1/1981 Grard ..................... D21H 13/40
                                                          162/134
(Continued)

FOREIGN PATENT DOCUMENTS

EP        3266429 B1 *  1/2019    ............. D21H 27/00
JP      H09-108261        4/1997
(Continued)

OTHER PUBLICATIONS

International Search Report for PCT/JP2016/056748 dated May 17, 2016.

*Primary Examiner* — Jose A Fortuna
(74) *Attorney, Agent, or Firm* — IPUSA, PLLC

(57) ABSTRACT

A method of manufacturing an absorbent article includes a paper making step in which, after forming a wet paper sheet from a source material and adding a fragrance material to the wet paper sheet, a pulp raw fabric sheet is obtained by dehydrating and drying the wet paper sheet; and a processing step of an absorbent article in which the pulp raw fabric sheet is defibrated and an absorbent body is manufactured by fiber stacking this defibrated fluff pulp.

6 Claims, 5 Drawing Sheets

(51) Int. Cl.
*D21H 23/04* (2006.01)
*D21H 23/22* (2006.01)
*A61F 13/53* (2006.01)
*D21H 27/00* (2006.01)
*A61F 13/15* (2006.01)
*A61F 13/531* (2006.01)
*D21H 23/28* (2006.01)

(52) U.S. Cl.
CPC ........ *A61F 13/15747* (2013.01); *A61F 13/53* (2013.01); *A61F 13/531* (2013.01); *D21H 21/14* (2013.01); *D21H 23/04* (2013.01); *D21H 23/22* (2013.01); *D21H 23/28* (2013.01); *D21H 27/00* (2013.01); *D21H 27/002* (2013.01); *A61F 2013/530007* (2013.01); *A61F 2013/8408* (2013.01); *A61F 2013/8435* (2013.01)

(58) Field of Classification Search
CPC ... D21H 27/30; A61F 13/15617; A61F 13/53; A61F 13/15626; A61F 13/15747; A61F 13/531; A61F 13/8405; A61F 2013/530007; A61F 2013/8408; A61F 2013/8435; D21F 11/14; D04H 1/593; D04H 1/732; D21B 1/066
See application file for complete search history.

(56) References Cited

U.S. PATENT DOCUMENTS

| | | | | |
|---|---|---|---|---|
| 4,425,186 A * | 1/1984 | May | ............... | A61L 15/48 162/158 |
| 4,969,976 A * | 11/1990 | Reed | ............... | D21C 9/18 162/164.3 |
| 5,484,896 A | 1/1996 | Naieni et al. | | |
| 5,776,308 A * | 7/1998 | Sears | ............... | D21C 9/005 162/158 |
| 6,296,737 B1 * | 10/2001 | Wu | ............... | A61L 15/18 162/158 |
| 6,416,624 B1 * | 7/2002 | Nielsen | ............... | B05D 1/025 162/155 |
| 6,503,233 B1 * | 1/2003 | Chen | ............... | A61F 13/47218 604/378 |
| 6,773,545 B2 * | 8/2004 | Tanner | ............... | D21B 1/066 162/20 |
| 6,797,116 B2 * | 9/2004 | Capizzi | ............... | D21H 21/56 118/257 |
| 7,842,163 B2 * | 11/2010 | Nickel | ............... | D21H 27/002 162/168.1 |
| 8,871,059 B2 * | 10/2014 | Jaakkola | ............... | D21C 9/007 162/208 |
| 8,916,024 B2 * | 12/2014 | Ban | ............... | D21H 17/20 162/72 |
| 9,347,182 B2 * | 5/2016 | Jaakkola | ............... | D21F 3/02 |
| 10,106,927 B2 * | 10/2018 | Nonni | ............... | D21C 9/144 |
| 2003/0056917 A1 * | 3/2003 | Jimenez | ............... | D21H 23/26 162/158 |
| 2004/0067214 A1 * | 4/2004 | Krautkramer | ........ | A61F 13/8405 424/76.3 |
| 2004/0099392 A1 * | 5/2004 | Liu | ............... | D21H 21/22 162/184 |
| 2004/0118533 A1 * | 6/2004 | Shannon | ............... | D21H 11/20 162/109 |
| 2004/0140048 A1 * | 7/2004 | Lindsay | ............... | A61F 13/47218 156/209 |
| 2005/0065487 A1 * | 3/2005 | Graef | ............... | A61F 13/5376 604/358 |
| 2006/0008621 A1 * | 1/2006 | Gusky | ............... | D04H 1/72 428/156 |
| 2006/0016570 A1 * | 1/2006 | Liu | ............... | D21H 23/50 162/158 |
| 2008/0268205 A1 * | 10/2008 | Vogel | ............... | D04H 1/64 428/156 |
| 2009/0029020 A1 | 1/2009 | Strassburger | | |
| 2010/0262098 A1 * | 10/2010 | Brusk | ............... | A61L 15/20 604/359 |
| 2011/0046587 A1 | 2/2011 | Meizelman | | |
| 2012/0297560 A1 * | 11/2012 | Zwick | ............... | D04H 1/587 15/104.93 |
| 2013/0037635 A1 * | 2/2013 | Singh | ............... | D21C 9/007 241/3 |
| 2013/0139980 A1 * | 6/2013 | Ban | ............... | D21H 17/20 162/74 |
| 2013/0158490 A1 * | 6/2013 | Caputi | ............... | A61F 13/8405 604/359 |
| 2013/0213594 A1 * | 8/2013 | Jaakkola | ............... | D21H 27/002 162/123 |
| 2013/0228948 A1 * | 9/2013 | Singh | ............... | D21H 11/16 264/103 |
| 2015/0038928 A1 * | 2/2015 | Tee, Jr. | ............... | A61L 15/46 604/359 |
| 2015/0238062 A1 * | 8/2015 | Baker | ............... | A47L 13/16 15/223 |
| 2018/0014986 A1 * | 1/2018 | Kurohara | ............... | D21H 21/14 |
| 2018/0363245 A1 * | 12/2018 | Luo | ............... | D21H 11/04 |

FOREIGN PATENT DOCUMENTS

| | | | | |
|---|---|---|---|---|
| JP | H09-510754 | 10/1997 | | |
| JP | 2000-509432 | 7/2000 | | |
| JP | 2001-172893 | 6/2001 | | |
| JP | 2008-546386 | 12/2008 | | |
| JP | 2013-177424 | 9/2013 | | |
| JP | 6234394 B2 * | 11/2017 | ............ | D21H 27/00 |
| WO | 99/04830 | 2/1999 | | |
| WO | 2008/104960 | 9/2008 | | |
| WO | WO-2013081955 A1 * | 6/2013 | ............... | D21C 9/18 |
| WO | WO-2016140341 A1 * | 9/2016 | ............ | D21H 27/00 |
| WO | WO-2019177826 A1 * | 9/2019 | ............... | D21F 1/66 |

* cited by examiner

ABSORBENT ARTICLE AND METHOD OF MANUFACTURING THE SAME

BACKGROUND OF THE INVENTION

1. Field of the Invention

The present invention relates to an absorbent article including a scented absorbent body such as a disposal diaper, an urine removal pad, an incontinence pad or a sanitary napkin, and a method of manufacturing the same.

2. Description of the Related Art

Conventionally, products are known by which fragrance or smell is generated when a wearer excretes so that smell of excretion is moderated, or custodians, guardians or the like can be aware of the excretion of the wearer.

For adding a fragrance material to an absorbent article, in order to suppress vaporization of fragrance components, the fragrance material is included in an inclusion material made of cyclodextrin or the like, and is coated or the like on the absorbent article. This is for preventing a loss of the fragrance material by vaporization, and also because qualities are required for a scented absorbent article such as generation of fragrance is reduced to be low before using, fragrance is strongly generated while using and after using and a masking effect or a harmonized effect can be obtained.

As a method of adding a fragrance material to an absorbent article, as illustrated in FIG. 8, a method of directly coating the fragrance material included in cyclodextrin on the absorbent body in a processing step of an absorbent article is the easiest way.

In addition, as illustrated in FIG. 9, there is a method of drying a inclusion reaction solution of a fragrance material and cyclodextrin to vaporize a non-included fragrance material, and collecting powders of the remaining fragrance material inclusion compound in a fragrance material preparing step, and thereafter, directly adding to the absorbent body or coating on the absorbent body after being mixed in an oil-based solvent in a manufacturing step of an absorbent article (see following Patent Document 1).

Further, following Patent Document 2 discloses a method of manufacturing a hydrogel forming absorbent polymer in which a fragrance material capable of emitting fragrance when a polymer is wet due to dynamic wetting force of the polymer is impregnated, including (i) a step of mixing a solid carrier and a fragrance material with a reaction intermediate product of a hydrogel forming absorbent polymer which is before a polymerization gel point of the hydrogel forming absorbent polymer, (ii) a step of forming a hydrogel forming absorbent polymer in which the fragrance material is impregnated and (iii) a step of drying the hydrogel forming absorbent polymer in which the fragrance material is impregnated.

PATENT DOCUMENTS

Patent Document 1: Japanese Laid-open Patent Publication No. 2013-177424
Patent Document 2: Japanese Patent No. 3222480

However, by the method of directly coating the fragrance material on the absorbent body illustrated in FIG. 8, the fragrance material is localized at an interlaminar between the absorbent body and the topsheet. Thus, there is a problem in that the fragrance material and the body fluid cannot effectively contact and the fragrance material hardly reacts with water. According to the technique disclosed in the above described Patent Document 1 as well, the same problem occurs because a complex of the fragrance material and cyclodextrin is adhered to an interlaminar that constitutes the absorbent article by the adhesive agent.

Further, by the method described in the above described Patent Document 1, the drying step for drying the inclusion reaction solution or the collecting step for collecting the powders of the remaining fragrance material inclusion compound are optionally necessary in the fragrance material preparing step. Thus, there is a problem that the manufacturing step becomes complicated.

Further, according to the technique described in the above described Patent Document 2, as the absorbent body includes the hydrogel forming absorbent polymer in which the fragrance material is impregnated, an inclusion property of the polymer is strong, gel blocking occurs, and a large amount of the fragrance material is necessary in order to generate the fragrance capable of being detected, and cost is increased.

SUMMARY OF THE INVENTION

Thus, the present invention is made in light of the above problems, and provides an absorbent article and a method of manufacturing the same in which contact efficiency between a fragrance material and body fluid is increased, fragrance can be effectively generated by a small amount of the fragrance material and a manufacturing step is simplified.

As a present invention of claim 1 for solving the above problem, there is provided an absorbent article including: an absorbent body in which a defibrated fluff pulp, defibrated from a pulp raw fabric sheet, is fiber stacked, a fragrance material being added to the pulp raw fabric sheet before being defibrated.

In the invention of claim 1, the fragrance material is previously added to the pulp raw fabric sheet before being defibrated, the pulp raw fabric sheet to which the fragrance material is added is defibrated, and the absorbent body is manufactured by fiber stacking the defibrated fluff pulp. Thus, the fragrance material is substantially uniformly dispersed in the entirety of the absorbent body, and contact efficiency between the fragrance material and body fluid when used is increased and fragrance is effectively generated by a small amount of the fragrance material.

Further, when the fragrance material is added to a wet paper sheet before drying in the paper making step of the pulp raw fabric sheet, a non-included fragrance material is also vaporized when drying the wet paper sheet in the paper making step. Thus, unlike the conventional method, it is unnecessary to provide a drying step of an inclusion reaction solution and a collecting step of collecting a remaining fragrance material inclusion compound in a preparing step of a fragrance material, and a manufacturing step can be simplified.

As a present invention of claim 2, there is provided absorbent article according to claim 1, wherein the fragrance material is included in an inclusion material consisting of one or more types selected from a group of cyclodextrin, xanthan gum, guar gum and pectin.

In the invention of claim 2, examples preferably used as an inclusion material of a fragrance material are raised.

As a present invention of claim 3, there is provided a method of manufacturing an absorbent article, including: a paper making step in which, after forming a wet paper sheet from a source material and adding a fragrance material to the wet paper sheet, a pulp raw fabric sheet is obtained by dehydrating and drying the wet paper sheet; and a processing step of an absorbent article in which the pulp raw fabric sheet is defibrated and an absorbent body is manufactured by fiber stacking this defibrated fluff pulp.

The invention of claim 3 is a first embodiment in which the fragrance material is added to the pulp raw fabric sheet, and the fragrance material is added to the wet paper sheet after forming the wet paper sheet. Thereafter, the pulp raw fabric sheet to which the fragrance material is added is defibrated in the processing step of the absorbent article, and the absorbent body is manufactured by fiber stacking the defibrated fluff pulp. With this, the fragrance material can be substantially uniformly dispersed in the entirety of the absorbent body, contact efficiency between a fragrance material and body fluid when using is increased, and the fragrance is effectively generated by a small amount of the fragrance material.

Further, the non-included fragrance material is vaporized at the same time with drying the wet paper sheet in the paper making step. Thus, it is unnecessary to additionally provide a drying step and a collecting step in a preparing step of the fragrance material, and the manufacturing step can be simplified.

As a present invention of claim 4, there is provided the method of manufacturing the absorbent article according to claim 3, wherein when the wet paper sheet is formed by a multi-layered cylinder paper machine, the fragrance material is added to a paper layer that is an intermediate layer among a plurality of stacked paper layers.

In the invention of claim 4, when the paper is made by a multi-layered cylinder paper machine, the fragrance material is added to a paper layer that is an intermediate layer among a plurality of wet paper sheets of stacked paper layers. With this, surface layers of the paper layers cover both sides of the intermediate layer to which the fragrance material is added, respectively. Thus, vaporization of the fragrance material is reduced, and a loss of the fragrance material or an adhesion of fragrance to a product that is subsequently manufactured can be prevented due to transition of the fragrance material to a paper making felt.

As a present invention of claim 5, there is provided a method of manufacturing an absorbent article, including: a paper making step in which, after forming a wet paper sheet from a source material in which a fragrance material is mixed, a pulp raw fabric sheet is obtained by dehydrating and drying the wet paper sheet; and a processing step of an absorbent article in which the pulp raw fabric sheet is defibrated and an absorbent body is manufactured by fiber stacking this defibrated fluff pulp.

The invention of claim 5 is a second embodiment in which the fragrance material is added to the pulp raw fabric sheet, and the fragrance material is previously mixed in the source material, and the wet paper sheet is formed by the source material in which the fragrance material is mixed.

As a present invention of claim 6, there is provided the method of manufacturing the absorbent article according to claim 5, wherein when the wet paper sheet is formed by a multi-layered cylinder paper machine, the fragrance material is mixed in a source material that forms a paper layer that is an intermediate layer among a plurality of staked paper layers.

In the invention of claim 6, when the wet paper sheet is formed by a multi-layered cylinder paper machine, the fragrance material is mixed in a source material that forms a paper layer that is an intermediate layer among a plurality of wet paper sheets of stacked paper layers.

As a present invention of claim 7, there is provided a method of manufacturing an absorbent article, including: a paper making step in which, after forming a wet paper sheet from a source material, a pulp raw fabric sheet is obtained by dehydrating and drying the wet paper sheet; and a processing step of an absorbent article in which, after adding a fragrance material to the pulp raw fabric sheet, the pulp raw fabric sheet is defibrated and an absorbent body is manufactured by fiber stacking this defibrated fluff pulp.

The invention of claim 7 is a third embodiment in which the fragrance material is added to the pulp raw fabric sheet, and the fragrance material is added to the pulp raw fabric sheet just before being defibrated after manufacturing the pulp raw fabric sheet by a normal paper making step.

As described above in detail, according to the invention, contact efficiency between a fragrance material and body fluid is increased, fragrance can be effectively generated by a small amount of the fragrance material, and a manufacturing step is simplified.

DETAILED DESCRIPTION OF THE PREFERRED EMBODIMENTS

Figure 1:
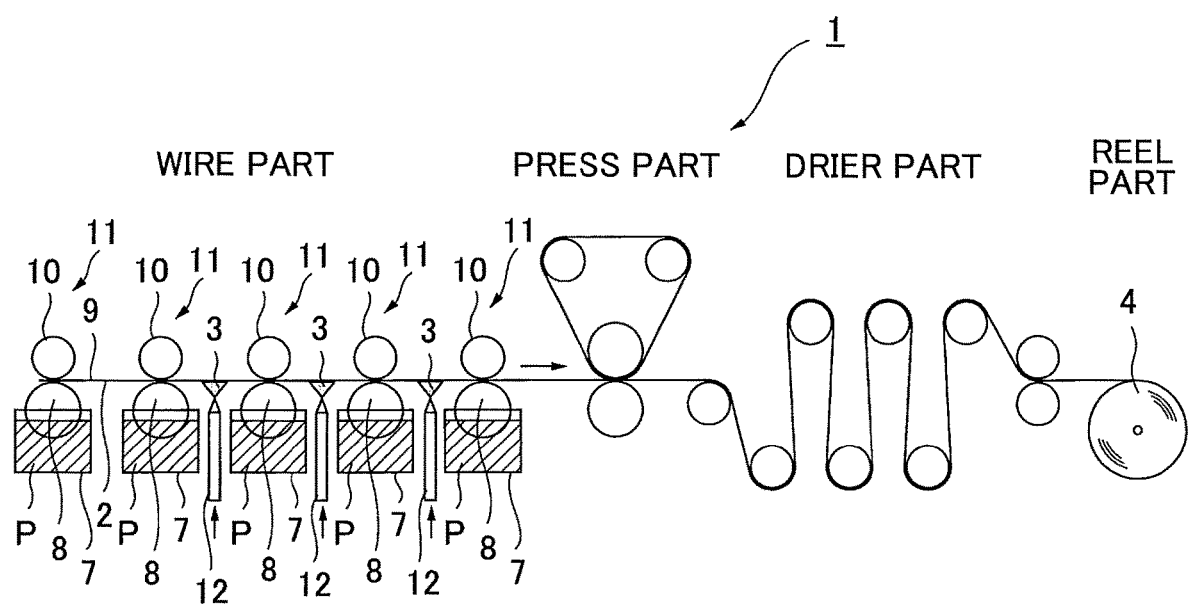
FIG. 1 is a schematic view illustrating a paper making step of a first embodiment.

Hereinafter, embodiments of the present invention are described in detail with reference to drawings.

An absorbent article of the invention has a structure in which an absorbent body made of a flocculated pulp or the like is provided between a liquid permeable topsheet made of a pored or non-pored nonwoven fabric, a perforated plastic sheet or the like and a liquid impermeable leak prevention sheet made of polyethylene or the like, and specifically, may be exemplified as a disposal diaper, a urine removal pad, an incontinence pad, a sanitary napkin or the like.

In the absorbent article, the absorbent body is structured by defibrating a pulp raw fabric sheet obtained in a paper making step, and fiber stacking this defibrated fluff pulp, wherein a fragrance material is added to the absorbent body by adding the fragrance material to the pulp raw fabric sheet before being defibrated.

As the fragrance material, it is preferable to use a configuration that generates fragrance at first after contacting body fluid, and does not generate the fragrance almost not at all before contacting the body fluid. Specifically, the fragrance material may be configured by one in which fragrance is generated by a reaction of a fragrance material component itself with water, one in which a fragrance material is included in an inclusion material or the like. Among these, it is preferable to use the one in which the fragrance material is included in the inclusion material in order to satisfy qualities required for a scented absorbent article, preventing a loss of the fragrance material due to vaporization, generation of fragrance is suppressed before using, the fragrance is strongly generated while using and after using and having a masking effect and a harmonized effect. The fragrance material is added to the absorbent body by a predetermined method.

As the fragrance material, either of a natural fragrance material and a synthetic fragrance material may be used, and these may be used in combination. As a specific example of the fragrance material, a natural fragrance material such as ambergris, benzoin, castoreum, civet, clove oil, galbanum, jasmine absolute, labdanum, mate, merirotto, mimosa, musk tonkin, myrrh, oakmoss (mousse de chêne), frankincense, angelica dahurica root, orris, patchouli, rosemary oil, sandalwood oil, vetiver oil or violet leaf absolute, various synthetic fragrance materials such as higher alcohol, aldehyde, benzaldehyde, benzoic acid, cinnamic acid, cinnamicaldehyde, cinnamyl alcohol, coumarin, ester, indole, ketone, salicylic acid and its related compound, terpenoid or vanillin, or a mixture of two or more of them may be raised, but not limited so. As the fragrance material, commercially available products may be widely used. It is preferable to use a fragrance material whose volatility is high as the fragrance material.

Further, it is possible to use a fragrance material having an odor eliminating effect or a harmonized fragrance material that generates fragrance harmonizing with unpleasant odor of the excretion by which new unpleasant smell is not generated as the fragrance material.

As the one in which the fragrance is generated by the reaction of the fragrance material component itself with water, an aqueous fragrance material (essence) or the like that is obtained by dissolving a fragrance material base into alcohol and water, and extracting and used for beverages may be used.

It is preferable that the fragrance material is included in an inclusion material consisting of one or more types selected from a group of cyclodextrin, xanthan gum, guar gum and pectin. In particular, it is preferable to use cyclodextrin because cyclodextrin is effective in adsorbing a smell component of the excretion in addition to emitting the fragrance.

As such, by adding the fragrance material to the pulp raw fabric sheet before being defibrated, following effects can be obtained.

First, according to the present absorbent article, the pulp raw fabric sheet to which the fragrance material is added is manufactured, and then, the absorbent body is manufactured by defibrating the pulp raw fabric sheet and fiber stacking the defibrated fluff pulp. Thus, the fragrance material can be substantially uniformly dispersed in the entirety of the absorbent body. Therefore, compared with a conventional one in which the fragrance material is localized at a predetermined interlaminar, contact efficiency between the fragrance material and the body fluid when using the absorbent article is increased, fragrance is easily generated, and the fragrance is effectively generated by a small amount of the fragrance material.

Figure 9:
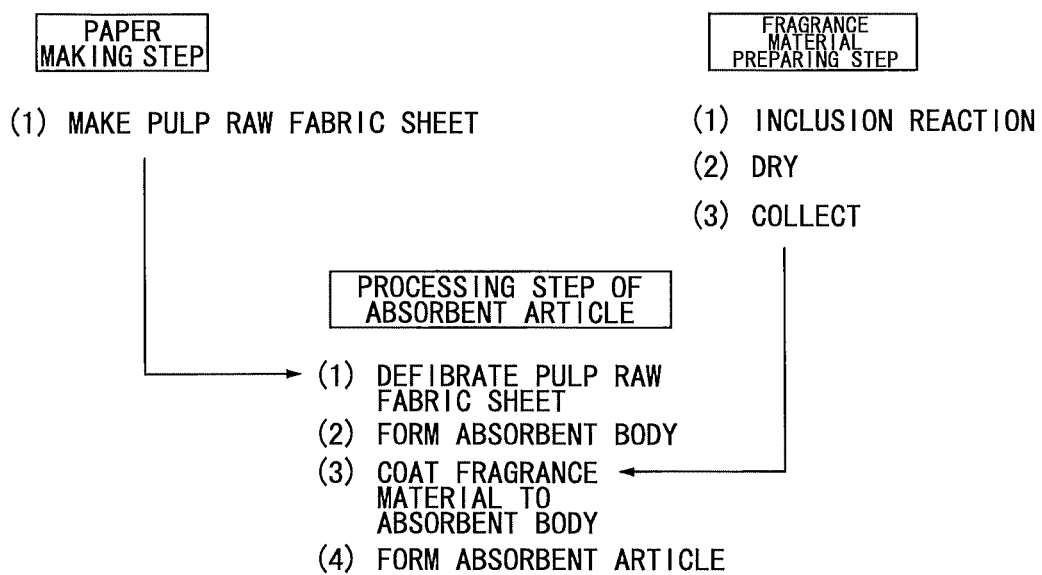
FIG. 9 is a flowchart (No. 2) illustrating a manufacturing procedure of a conventional absorbent article.

Second, if the fragrance material is added to a wet part before drying a wet paper sheet in a paper making step of the pulp raw fabric sheet, a non-included fragrance material can be vaporized at the same time in drying the wet paper sheet in the paper making step. Thus, it is unnecessary to additionally provide a drying step of drying the inclusion reaction solution and a collecting step of collecting the remaining fragrance material inclusion compound in the fragrance material preparing step (see FIG. 9), and the manufacturing step can be simplified.

In this specification, the "inclusion material" means a material that has a function to include (capture) another material in an internal space of a molecular structure of itself, and the "inclusion compound" means a material under a state that the inclusion material includes a material to be included such as a fragrance material.

Next, a method of manufacturing an absorbent body of a method of manufacturing an absorbent article is described in detail.

First Embodiment

Figure 2:
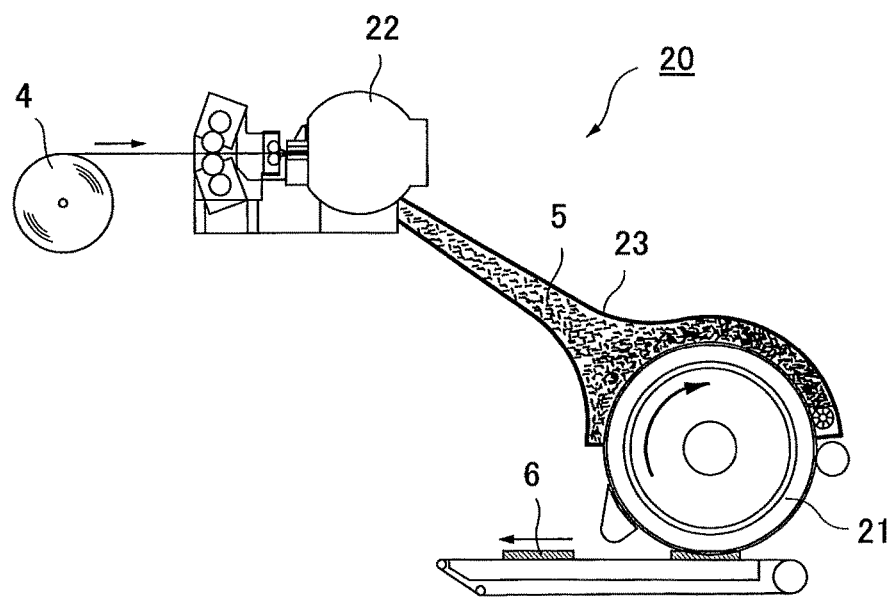
FIG. 2 is a schematic view illustrating an absorbent body manufacturing apparatus.
Figure 3:
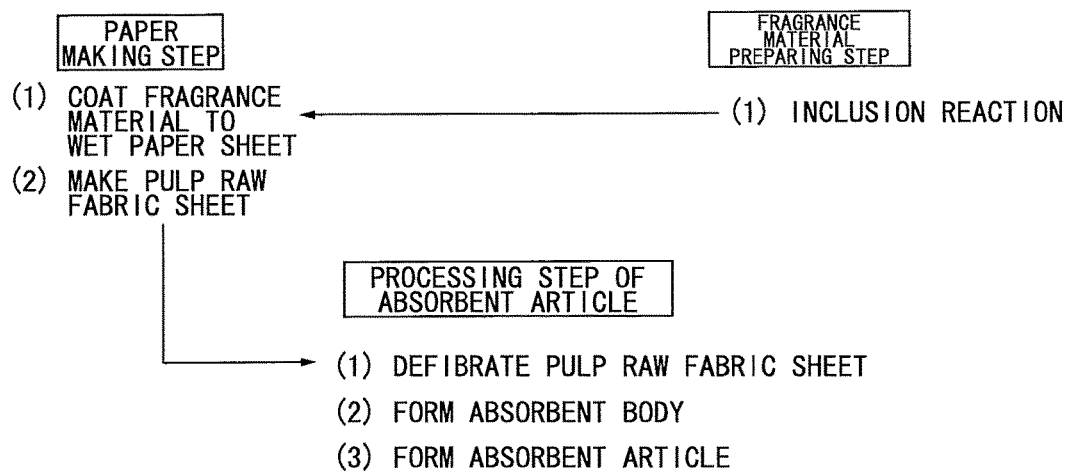
FIG. 3 is a flowchart illustrating a manufacturing procedure of an absorbent article of the first embodiment.

A method of manufacturing an absorbent article of a first embodiment includes, as illustrated in FIG. 1 and FIG. 3, a paper making step performed by a cylinder paper machine 1 in which a wet paper sheet 2 is formed from a source material P and, after adding a fragrance material 3 to the wet paper sheet 2, a pulp raw fabric sheet 4 is obtained by dehydrating and drying the wet paper sheet 2, and as illustrated in FIG. 2 and FIG. 3, a processing step of an absorbent article performed by an absorbent body manufacturing apparatus 20 in which the pulp raw fabric sheet 4 is defibrated (fluffed) and an absorbent body 6 is manufactured by fiber stacking this defibrated fluff pulp 5. Further, as illustrated in FIG. 3, the method of manufacturing further includes a fragrance material preparing step in which aqueous solution of the fragrance material and an inclusion material is mixed in a stirring tank and the fragrance material is coated by the inclusion material.

As the paper machine used in the paper making step, a known paper machine such as a cylinder paper machine or a wire paper machine (Fourdrinier paper machine) may be used. Here, as illustrated in FIG. 1, it is preferable to use the cylinder paper machine 1.

As illustrated in FIG. 1, the cylinder paper machine 1 includes a wire part, a press part, a drier part and a reel part, and one that has a basic structure same as that of a conventional one may be used.

In the wire part of the cylinder paper machine 1, when simply described, multi-stage cylinder paper making parts 11, each including a vat 7 which is a tank whose upper surface is open, and in which a source material P made of a fiber material such as a pulp, which becomes a source material of the absorbent body 6, is dispersed in water and reserved, a cylinder mold 8 which is rotated in a source material liquid in the vat 7 and forms a wet paper sheet on a wire at a surface, and a couch roll 10 which transfers the wet paper sheet formed at the surface of the cylinder mold 8 to a paper making felt 9, are provided along a flowing direction, preferably greater than or equal to three stages, for the illustrated example, five stages. By providing the multi-stage cylinder paper making parts 11, the pulp raw fabric sheet 4 of a multi-layer in which a paper layer transferred from the cylinder mold 8 of each stage is stacked in order can be obtained.

As illustrated in FIG. 1, when the wet paper sheet 2 is formed by the multi-layered cylinder paper machine 1, it is preferable that the fragrance material 3 is added to a paper layer which is an intermediate layer among the stacked multi-layered paper layers. This means, for the illustrated example, in which five stages of the cylinder paper making parts 11, 11 . . . are provided, it is preferable that the fragrance material 3 is added to the paper layers formed by second to fourth stages of the cylinder paper making parts 11 from upstream, respectively, and it is preferable that the fragrance material 3 is not added to the paper layers formed by the most upstream first stage and the most downstream fifth stage cylinder paper making parts 11, respectively.

With this, both surfaces of the intermediate paper layers to each of which the fragrance material 3 is added are covered by the paper layers at surfaces. Thus, vaporization of the fragrance material 3 can be reduced, and a loss of the fragrance material or an adhesion of fragrance to a product that is subsequently manufactured can be prevented due to transition of the fragrance material to the paper making felt 9.

For adding the fragrance material 3 to the wet paper sheet, it is preferable that the fragrance material 3 is mixed with water or an oil-based solvent, and a fragrance material containing solution in which the inclusion material is added is prepared in a separately provided fragrance material preparing step. Then, as illustrated in FIG. 1, it is preferable that the fragrance material containing solution is spray coated from an injection nozzle 12.

A constitution example of the fragrance material containing solution may be 88.4 wt. % of water, 10.3 wt. % of α-cyclodextrin, 1 wt. % of the fragrance material and 0.3 wt. % of xanthan gum. Here, by adding xanthan gum with α-cyclodextrin as the inclusion material, inclusion property of the fragrance material in α-cyclodextrin is increased, and as a moisture content is temporarily increased immediately after it is coated on the wet paper sheet 2 which contains water, the fragrance material can be prevented from being removed.

As a specific example of a coating amount of the fragrance material 3, when the pulp raw fabric sheet 4, 130 g/m$^2$ per layer, and 650 g/m$^2$ in total of five layers, is made by the cylinder paper machine 1 including the five stages of the cylinder paper making parts 11, 13 g/m$^2$ to each, 39 g/m$^2$ in total, of the fragrance material containing solution may be spray coated to the intermediate three paper layers of the wet paper sheet 2. With this amount, 0.36 g (0.0036 g of the fragrance material itself) of the fragrance material containing solution is added to weight of 6 g of an absorbent body, which is used for a normal baby disposal diaper. However, the present technique is not limited to a baby disposal diaper, and is effective for a widely and general disposal diaper for adult or the like.

Next, a manufacturing step of the absorbent body 6 of the processing step of the absorbent article is described in detail. For manufacturing the absorbent body 6, as illustrated in FIG. 2, the absorbent body manufacturing apparatus 20 is used. The absorbent body manufacturing apparatus 20 includes a fiber stacking rotating drum 21 provided with a plurality of concave portions for accumulating fiber stacking at an outer peripheral surface with appropriate distances in a circumferential direction, a defibrating apparatus 22 for fluffing the pulp raw fabric sheet 4 and a fiber supplying path 23 for transferring a fluff pulp 5 fluffed by the defibrating apparatus 22 to the fiber stacking rotating drum 21 along airflow. Here, although not illustrated in the drawings, an input port for inputting a polymer may be provided in the fiber supplying path 23, and a predetermined percentage of polymer particles or the like may be mixed in the fluff pulps 5.

In the absorbent body manufacturing apparatus 20, a sheet fed from the pulp raw fabric sheet 4 made in the paper making step is introduced into the defibrating apparatus 22, and is finely fluffed. The fluffed fluff pulp 5 is transferred to the downstream fiber stacking rotating drum 21 along the airflow in a casing that constitutes the fiber supplying path 23 by an aspiration function from the fiber stacking rotating drum 21, and accumulated in the concave portions for accumulating fiber stacking formed in the fiber stacking rotating drum 21.

As the absorbent body 6 manufactured by using the absorbent body manufacturing apparatus 20 is formed by, after finely fluffing the pulp raw fabric sheet 4 to which the fragrance material 3 is added by the defibrating apparatus 22, accumulating it, the fragrance material 3 is substantially uniformly dispersed in the entirety of the thickness direction and the planer direction of the absorbent body 6.

Second Embodiment

Figure 4:
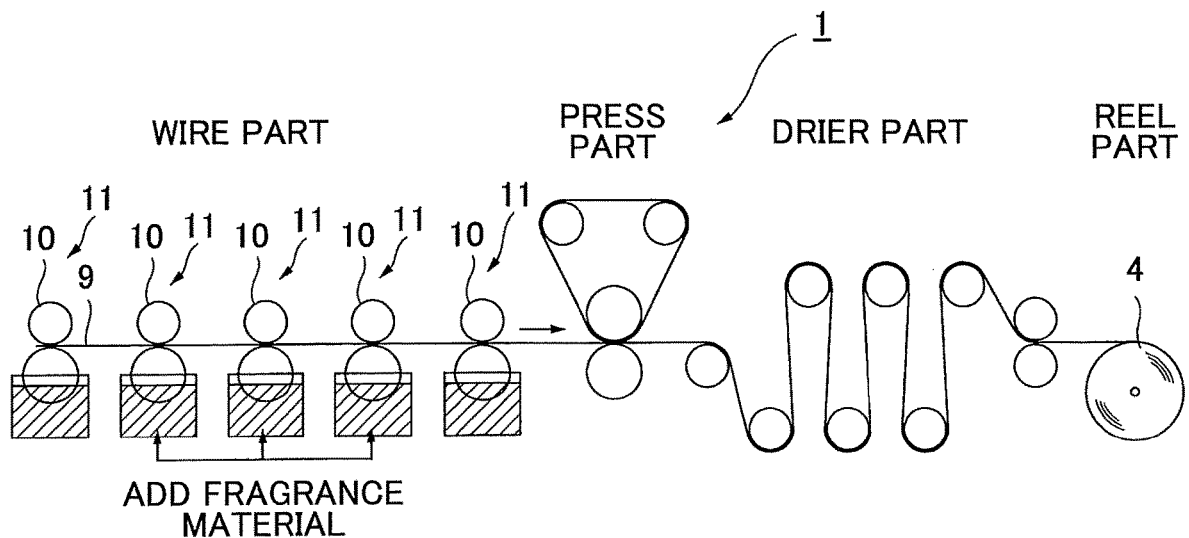
FIG. 4 is a schematic view illustrating a paper making step of a second embodiment.
Figure 5:
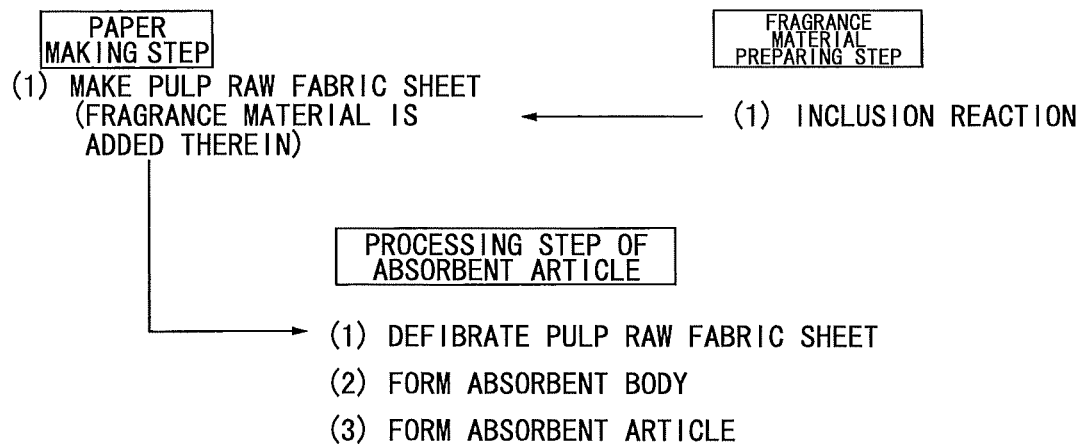
FIG. 5 is a flowchart illustrating a manufacturing procedure of an absorbent article of the second embodiment.

As illustrated in FIG. 4 and FIG. 5, a method of manufacturing an absorbent article of a second embodiment includes a paper making step in which a fragrance material 3 is previously mixed in a source material liquid, a wet paper sheet 2 is formed from a source material P in which the fragrance material 3 is mixed, and thereafter, a pulp raw fabric sheet 4 is obtained by dehydrating and drying the wet paper sheet 2, and a processing step of an absorbent article in which the pulp raw fabric sheet 4 is defibrated and an absorbent body 6 is manufactured by fiber stacking this defibrated fluff pulp 5.

As illustrated in FIG. 4, when the cylinder paper machine 1 is used, the fragrance material 3 is added in the source material P reserved in the vat 7 of each of the cylinder paper making parts 11. For adding the fragrance material 3, similar to the above described first embodiment, the fragrance material 3 is added after the fragrance material 3 is mixed with water or an oil-based solvent, and a fragrance material containing solution in which the inclusion material is added is prepared in a fragrance material preparing step.

With this, the fragrance material 3 is added to the wet paper sheet 2 in a uniformly dispersed manner. Thus, by manufacturing the absorbent body 6 by defibrating the pulp raw fabric sheet 4, the fragrance material 3 can be furthermore uniformly dispersed in the absorbent body 6.

As illustrated in FIG. 4, when the multi-layered cylinder paper machine 1 in which the five stages of the cylinder paper making parts 11, 11 are provided is used, it is preferable that the fragrance material 3 is added to the vats 7 of the intermediate second to fourth stages of the cylinder paper making parts 11, 11 . . . from upstream, respectively, except the most upstream first stage and the most downstream fifth stage cylinder paper making parts 11, 11. With this, similar to the above described first embodiment, vaporization of the fragrance material 3 can be reduced, and transition of the fragrance material to the paper making felt 9 can be prevented.

As a constitution example of the fragrance material containing solution to which the fragrance material 3 is added may be the same as that of the above described first embodiment. An adding amount of the fragrance material containing solution with respect to the 1% source material P may be 2.0 to 4.0 kg/t, preferably approximately 3.0 kg/t. When an amount of 3.0 kg/t of the fragrance material 3 configured by the above described percentage is added to the 1% source material P, 1.08 g of the fragrance material containing solution 3 is added to 6 g of an absorbent body, which is used for a normal baby disposal diaper. However, the present technique is not limited to a baby disposal diaper, and is effective for a widely and general disposal diaper for adult or the like.

Third Embodiment

Figure 6:
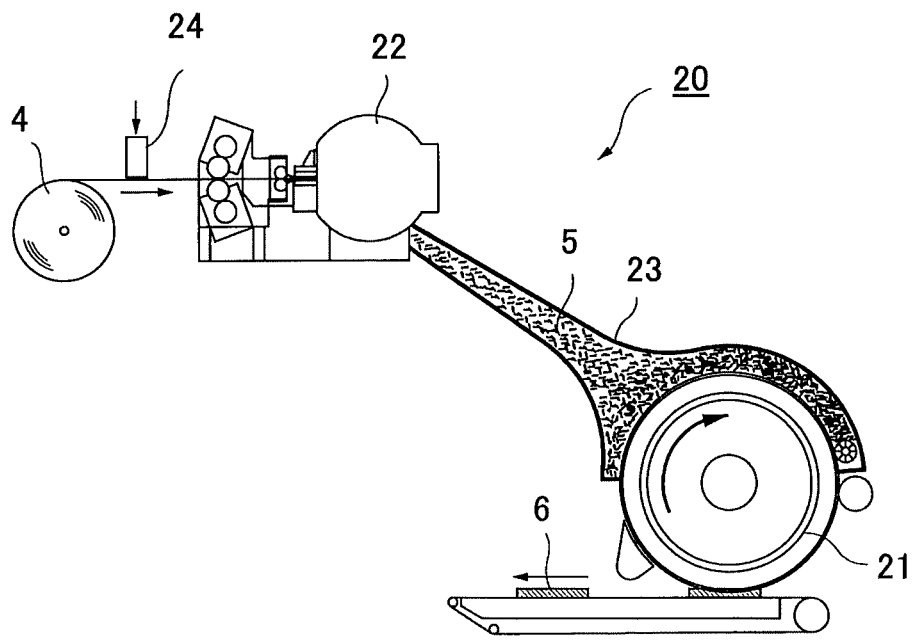
FIG. 6 is a schematic view illustrating an absorbent body manufacturing apparatus of a third embodiment.
Figure 7:
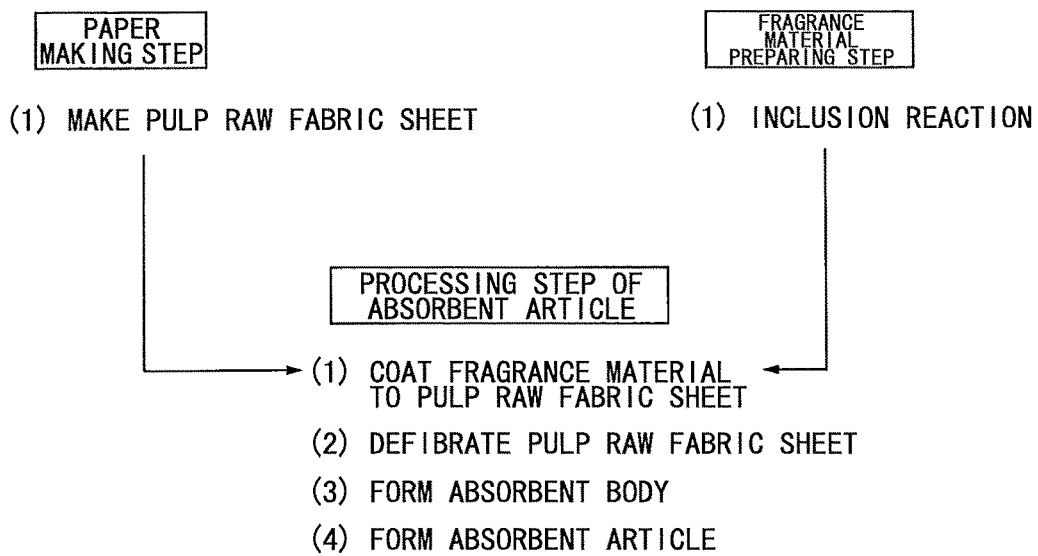
FIG. 7 is a flowchart illustrating a manufacturing procedure of an absorbent article of the third embodiment.

As illustrated in FIG. 6 and FIG. 7, a method of manufacturing an absorbent article of a third embodiment includes a paper making step in which a wet paper sheet 2 is formed from the source material P, and thereafter, a pulp raw fabric sheet 4 is obtained by dehydrating and drying the wet paper sheet 2, and a processing step of an absorbent article in which the pulp raw fabric sheet 4 is defibrated after adding a fragrance material 3 to the pulp raw fabric sheet 4, and an absorbent body 6 is manufactured by fiber stacking this defibrated fluff pulp 5.

According to the method of manufacturing, as the fragrance material 3 is added just before defibrating the pulp raw fabric sheet 4 after manufacturing the pulp raw fabric sheet 4 by a normal paper making step, it is relatively easy to add the fragrance material 3 to the pulp raw fabric sheet 4. Thus, the manufacturing step can be simplified.

Further, in a defibrating step of the pulp raw fabric sheet 4 to which the fragrance material 3 is added, a drying effect by which a non-included fragrance material is vaporized can be expected. This means that a slight drying effect can be obtained in the defibrating step of the pulp raw fabric sheet 4 and in a step in which the finely defibrated fluff pulp 5 is transferred to a fiber stacking drum along airflow. Although this drying effect is not high compared with the above described first embodiment and the second embodiment, this drying effect is higher than a normal manufacturing method. As illustrated in examples (Table 1), which will be described later in detail, this is apparent from facts that the strength of the fragrance before using in example 5 (third embodiment) is not low as those of example 1 (first embodiment) and examples 2 to 4 (second embodiment) but is lower (1.0→0.8) than those of comparative examples 1 and 2.

It is preferable that the fragrance material 3 is added by preparing a fragrance material containing solution in which the fragrance material 3 is mixed in water or the like and spray coating the fragrance material containing solution by a coating applicator 24 for uniformly dispersing the fragrance material on a surface of the pulp raw fabric sheet 4. At this time, as there is a concern that mold is generated because a water content of the manufactured absorbent body 6 is increased due to coating the fragrance material containing solution, it is preferable to add an antiseptic agent to the fragrance material containing solution to prevent generation of the mold.

A constitution example of the fragrance material containing solution may be, 86.9 wt. % of water, 10.3 wt. % of α-cyclodextrin, 1 wt. % of the fragrance material and 1.8 wt. % of the antiseptic agent. A coating amount of the fragrance material containing solution may be 39 g/m². With this amount, 0.36 g of the fragrance material containing solution is added to each 6 g of an absorbent body, which is used for a normal baby disposal diaper. However, the present technique is not limited to a baby disposal diaper, and is effective for a widely and general disposal diaper for adult or the like.

EXAMPLES

As illustrated in Table 1, in accordance with the method of manufacturing the absorbent body of each of the above embodiments, absorbent bodies were manually manufactured (hand making a pulp raw fabric sheet, fluffing the sheet, forming an absorbent body, adding a fragrance material in a respective step), and strengths of fragrance before and after using were comparatively assessed.

As the fragrance material containing solution, "A solution" consisting of 88.4% of water, 10.3% of α-cyclodextrin, 1.0% of a fragrance material and 0.3% of xanthan gum, and "B solution" consisting of 86.9% of water, 10.3% of α-cyclodextrin, 1.0% of a fragrance material and 1.8% of an antiseptic agent were used. The "A solution" was used in each of examples 1 to 4 and comparative example 1 and the "B solution" was used in each of example 5 and comparative example 2.

A process of manufacturing each of the absorbent bodies was as follows.

Process 1: (1) 1% solution was prepared by suspending NBKP in ion-exchanged water. (2) A hand-made sheet (pulp raw fabric sheet) whose basic weight was 130 g/m² was manufactured by a rectangular sheet former (25 cm×25 cm) (1% solution of NBKP was stirred in a filtering layer and filtered→the fragrance material containing solution was dropped on the entirety of the sheet by a dropper→pressed and dried by a drier). (3) The sheet was fluffed by a kitchen mixer in a flocculated manner. (4) An absorbent body with a width of 10 cm×a length of 35 cm×a thickness of 1 cm was manufactured by mixing 6 g of the fluff pulp and 10 g of an absorbent polymer. (5) The absorbent body was covered by a crape paper whose basic weight was 18 g/m². (6) Its outer peripheral was further covered by a hydrophilic nonwoven fabric whose basic weight was 18 g/m².

Process 2: (1) 1% solution was prepared by suspending NBKP in ion-exchanged water. (2) A fragrance material containing solution was added to the solution. (3) A hand-made sheet (pulp raw fabric sheet) whose basic weight was 130 g/m² was manufactured by a rectangular sheet former (25 cm×25 cm) (1% solution of NBKP including the fragrance material was stirred and filtered in a filtering layer→pressed and dried by a drier). (4) Hereinafter, the same as (3) to (6) of the process 1.

Process 3: (1) 1% solution was prepared by suspending NBKP in ion-exchanged water. (2) A hand-made sheet (pulp raw fabric sheet) whose basic weight was 130 g/m² was manufactured by a rectangular sheet former (25 cm×25 cm) (1% solution pf NBKP was stirred and filtered in a filtering layer→pressed and dried by a drier→the fragrance material containing solution was dropped on the entirety of the sheet by a dropper). (3) Hereinafter, the same as (3) to (6) of the process 1.

Process 4: (1) 1% solution was prepared by suspending NBKP in ion-exchanged water. (2) A hand-made sheet (pulp raw fabric sheet) whose basic weight was 130 g/m² was manufactured by a rectangular sheet former (25 cm×25 cm) (1% solution of NBKP was stirred in a filtering layer and filtered→pressed and dried by a drier). (3) The sheet was fluffed by a kitchen mixer in a flocculated manner. (4) 6 g of the fluff pulp and 10 g of an absorbent polymer were mixed, and an absorbent body with a width of 10 cm×a length of 35 cm×a thickness of 1 cm was manufactured. (5) The fragrance material containing solution was dropped on the entirety of the absorbent body by a dropper. (6) The absorbent body was covered by a crape paper whose basic weight was 18 g/m². (7) Its outer peripheral was further covered by a hydrophilic nonwoven fabric whose basic weight was 18 g/m².

In the above processes 1 to 3, after manufacturing the hand-made sheet (pulp raw fabric sheet), the sheet was stood still in a thermostatic chamber at a temperature of 25° C. and a humidity of 50% for a week. Further, in the above process 4, after covering by the hydrophilic nonwoven fabric, the absorbent body was stood still in a thermostatic chamber at a temperature of 25° C. and a humidity of 50% for a week.

For a method of assessing strength of fragrance, each strength of fragrance before using and strength of the fragrance after using was sensory evaluated, and while setting the strength of the fragrance before using of comparative example 1 as 1.0, others were comparatively assessed.

As a result, as illustrated in Table 1, for each of examples 1 to 5 of the invention, compared with comparative examples 1 and 2 in each of which the fragrance material was sprayed on the absorbent body, it was confirmed that the fragrance before using was suppressed, and a sufficient fragrance was sensed after using. Further, for example 5 of the invention, a result was obtained in which the fragrance stronger than the strength of the fragrance after using of comparative example 2 was generated by effectively reacting with water.

TABLE 1

Figure 8:
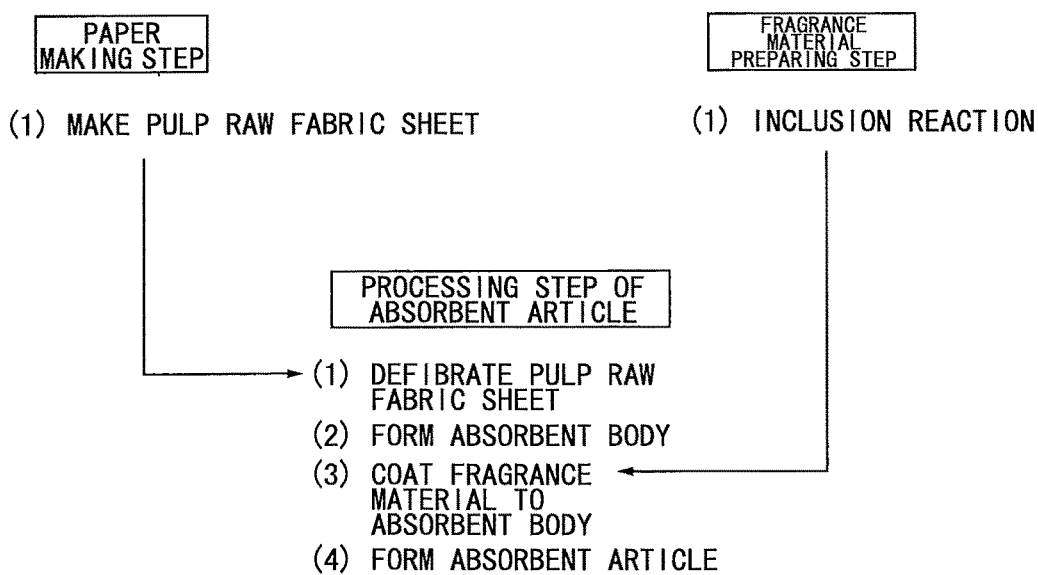
FIG. 8 is a flowchart (No. 1) illustrating a manufacturing procedure of a conventional absorbent article.

|  | EXAMPLE 1 | EXAMPLE 2 | EXAMPLE 3 | EXAMPLE 4 | EXAMPLE 5 | COMPARATIVE EXAMPLE 1 | COMPARATIVE EXAMPLE 2 |
|---|---|---|---|---|---|---|---|
| PROCESS OF MANUFACTURING ABSORBENT BODY | PROCESS 1 | PROCESS 2 | | | PROCESS 3 | PROCESS 4 | |
| REFERENCE DRAWING | FIG. 3 | FIG. 5 | | | FIG. 7 | FIG. 8 | |
| FRAGRANCE MATERIAL CONTAINING SOLUTION | | A SOLUTION | | | B SOLUTION | A SOLUTION | B SOLUTION |
| ADDED AMOUNT OF FRAGRANCE MATERIAL CONTAINING SOLUTION TO EACH ABSORBENT BODY (g) | 0.36 | 0.72 | 1.08 | 1.44 | 0.36 | 0.36 | 0.36 |
| PERCENTAGE OF WEIGHT OF FRAGRANCE MATERIAL ITSELF WITH RESPECT TO A TOTAL WEIGHT OF PULP AND POLYMER (%) | 0.023 | 0.045 | 0.068 | 0.090 | 0.023 | 0.023 | 0.023 |
| COMPARATIVE ASSESSMENT OF STRENGTH OF FRAGRANCE BEFORE USING | 0.3 | 0.2 | 0.2 | 0.6 | 0.8 | 1.0 | 1.0 |
| COMPARATIVE ASSESSMENT OF STRENGTH OF FRAGRANCE AFTER USING | 1.6 | 1.4 | 1.5 | 1.7 | 1.8 | 1.6 | 1.5 |

The strength of the fragrance before using was assessed by introducing each of the absorbent bodies manufactured by the above processes in a zippered plastic bag, opening a zip after five minutes from closing the zip, and smelling the fragrance in the bag to evaluate the strength of the fragrance by 5 grades (0, 0.5, 1.0, 1.5, 2.0 points). This was performed by 30 evaluators (N=30), and an average value was used as the strength of the fragrance before using.

The strength of the fragrance after using is strength of the fragrance on the assumption that the absorbent body is wet by body fluid when the absorbent article is worn, and was assessed by causing the entirety of each of the absorbent bodies manufactured by the above processes to uniformly absorb 150 cc of ion-exchanged water, introducing it in a zippered plastic bag, opening a zip after five minutes from closing the zip, and smelling the fragrance in the bag to evaluate the fragrance by 5 grades (0, 0.5, 1.0, 1.5, 2.0 points). This was performed by 30 evaluators (N=30), and an average value was used as the strength of the fragrance after using.

The comparative assessment of the strength of the fragrance was performed by converting each of the strengths of the fragrance (average values) before and after using by a proportion while setting the strength of the fragrance before using of comparative example 1 to be 1.0. When the value is higher, that indicates that the fragrance is stronger.

1 . . . cylinder paper machine, 2 . . . wet paper sheet, 3 . . . fragrance material, 4 . . . pulp raw fabric sheet, 5 . . . fluff pulp, 6 . . . absorbent body, 7 . . . vat, 8 . . . cylinder mold, 9 . . . paper making felt, 10 . . . couch roll, 11 . . . cylinder paper making part, 20 . . . absorbent body manufacturing apparatus, 21 . . . fiber stacking rotating drum, 22 . . . defibrating apparatus, 23 . . . fiber supplying path, P . . . source material

What is claimed is:
1. A method of manufacturing an absorbent article, comprising:
   forming a wet paper sheet from a source material;
   adding a fragrance material solution to the wet paper sheet, said fragrance material solution containing 88.4 wt. % of water, 10.3 wt. % of α-cyclodextrin, 1 wt. % of fragrance material and 0.3 wt. % of xanthan gum;
   dehydrating and drying the wet paper, thereby obtaining a pulp raw fabric sheet;
   defibrating the pulp raw fabric sheet; and
   accumulating defibrated fluff pulp, thereby manufacturing an absorbent body.

2. The method of manufacturing the absorbent article according to claim 1, wherein when the wet paper sheet is formed by a multi-layered cylinder paper machine, the fragrance material is added to a paper layer that is an intermediate layer among a plurality of stacked paper layers.

3. The method of manufacturing the absorbent article according to claim 1, wherein the accumulating step is performed by accumulating the defibrated fluff pulp in concave portions provided at an outer peripheral surface of a rotating drum.

4. The method of manufacturing the absorbent article according to claim 1, wherein an adding amount of the fragrance material solution with respect to the 1% source material is 2.0 to 4.0 kg/t.

5. The method of manufacturing the absorbent article according to claim 4, wherein the adding amount of the fragrance material solution with respect to the 1% source material is 3.0 kg/t.

6. A method of manufacturing an absorbent article, comprising:
   forming a wet paper sheet from a source material;
   dehydrating and drying the wet paper, thereby obtaining a pulp raw fabric sheet;
   adding a fragrance material solution to the pulp raw fabric sheet, said fragrance material solution containing 86.9 wt. % of water, 10.3 wt. % of α-cyclodextrin, 1 wt. % of fragrance material and 1.8 wt. % of antiseptic agent;
   defibrating the pulp raw fabric sheet; and
   accumulating defibrated fluff pulp thereby manufacturing an absorbent body.

\* \* \* \* \*